(12) United States Patent
Tanaka et al.

(10) Patent No.: US 6,183,697 B1
(45) Date of Patent: *Feb. 6, 2001

(54) PARTICLE MEASURING APPARATUS

(75) Inventors: Yousuke Tanaka; Masakazu Fukuda, both of Kobe; Junzo Yamamoto, Kasai, all of (JP)

(73) Assignee: Sysmex Corporation, Hyogo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/084,418

(22) Filed: May 27, 1998

(30) Foreign Application Priority Data

May 27, 1997 (JP) ..................................................... 9-137137
Jun. 3, 1997 (JP) ..................................................... 9-145442

(51) Int. Cl.$^7$ ........................................................ G01N 21/64
(52) U.S. Cl. ............................ 422/82.05; 422/117; 356/72

(58) Field of Search .................................. 422/62, 82.08, 422/82.13, 110, 111, 112, 82.09, 117, 119; 356/72, 73; 73/61.64, 61.73, 861.05

(56) References Cited

U.S. PATENT DOCUMENTS

| | | | |
|---|---|---|---|
| 4,352,558 | * 10/1982 | Eisert | 359/39 |
| 5,245,318 | * 9/1993 | Tohge et al. | 356/338 |
| 5,517,870 | * 5/1996 | Kurimura et al. | 73/865.5 |

FOREIGN PATENT DOCUMENTS 5-87779   12/1993   (JP) .

* cited by examiner

*Primary Examiner*—Jeffrey Snay

(57) ABSTRACT

A particle measuring apparatus surrounds a sample with a sheath liquid to hydrodynamically converge and flow them, and optically measures a particle in the sample to obtain a signal data of the particle. The apparatus provides a monitoring section for comparing a pulse width of the signal data as obtained, with a predetermined standard value to obtain a comparison value and monitoring a flow rate of the sheath liquid based on the comparison value.

12 Claims, 7 Drawing Sheets

Transition of Fscw Average Value for Each Batch (n=20)

PARTICLE MEASURING APPARATUS

CROSS-REFERENCES TO RELATED APPLICATIONS

This application is related to Japanese Patent Applications No. HEI 09-137137 filed on May 27, 1997 and No. HEI 09-145442 filed on Jun. 3, 1997 whose priority is claimed under 35 USC §119, the disclosure of which is incorporated herein by reference in its entirety.

BACKGROUND OF THE INVENTION

1. Field of the Invention

The present invention relates to a particle measuring apparatus, and more particularly to a particle measuring apparatus for surrounding a sample with a sheath liquid to hydrodynamically converge and flow them by giving them a predetermined pressure difference, and making a measurement based on a signal data from a particle in the sample.

2. Description of the Background Art

A particle measuring apparatus of this type, such as a flow cytometer, is an apparatus for allowing the sample and the surrounding sheath liquid such as a physiological saline solution to flow at a high speed in a flow cell by giving them a predetermined pressure difference, converging the flow hydrodynamically to form a sample flow, applying a laser light to specimen particles flowing one by one at a converging position, detecting a scattered light from a solid component of the specimen particle by a photodetector, and analyzing a property, structure, and the like of the specimen particle from an obtained pulse waveform. Such an apparatus is used in the fields of cytology, hematology, oncology, genetics, and the like. Naturally, an accurate measurement of particles in the sample would be difficult if impurities (for example, a bacterium or an air bubble in the case where the objects of measurement are bacteria in a urine) are mingled in the sheath liquid.

In order to solve this problem, a method is known in which the impurities are removed by providing a filter section between a flow cell and a sheath liquid pressuring section which supplies a pressurized sheath liquid to the flow cell. However, when the higher pressure side of the filter section is clogged with impurities, the filtration efficiency decreases and the filter section must be exchanged. Therefore, a method is known in which a pressure sensor is provided downstream of the filter section to check the decrease in pressure of the sheath liquid, thereby monitoring the clogging of the filter section or, further, adjusting and controlling the pressurizing force of the sheath liquid pressurizing section on the basis of a pressure detection signal of the pressure sensor (for example, see Japanese Examined Patent Publication No. HEI 05(1993)-87779).

However, even if the clogging of the filter section can be monitored in this way by providing a pressure sensor downstream of the filter section, there is a problem that the pressure change caused by clogging is very small, so that, when the pressure change has been detected, the filter section is almost completely clogged, rendering the filter section impractical. Also, it is known that, even if there is no clogging in the filter section and the pressurizing force is constant, the flow rate (amount of flow per unit period of time) changes greatly because of the change in kinematic viscosity of the liquid due to the change in temperature. Therefore, at present, it is difficult to maintain a constant flow rate of the sheath liquid by monitoring or controlling the filter section in accordance with the pressure change. Also, very high costs of the pressure sensors and the pressure controlling means (for example, automatically controlled air pressurizing device) are problems.

SUMMARY OF THE INVENTION

Therefore, one of the major objects of the present invention is to provide a particle measuring apparatus having a simple construction and being capable of securely monitoring or stabilizing a fluctuation of the flow rate of the sheath liquid, thereby allowing the apparatus to have a highly reliable measurement accuracy.

Another major object of the present invention is to provide a particle measuring apparatus capable of delaying the clogging of the filter section, which is a cause of the fluctuation in the flow rate of the sheath liquid, in addition to monitoring the flow rate of the sheath liquid, thereby extending the life span of the filter section and allowing the apparatus to have a further highly reliable measurement accuracy.

Accordingly, the present invention provides a particle measuring apparatus for surrounding a sample with a sheath liquid to hydrodynamically converge and flow them, and optically measuring a particle in the sample to obtain a signal data of the particle, the apparatus providing a monitoring section for comparing a pulse width of the signal data as obtained, with a predetermined standard value to obtain a comparison value and monitoring a flow rate of the sheath liquid based on the comparison value.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Figure 1:
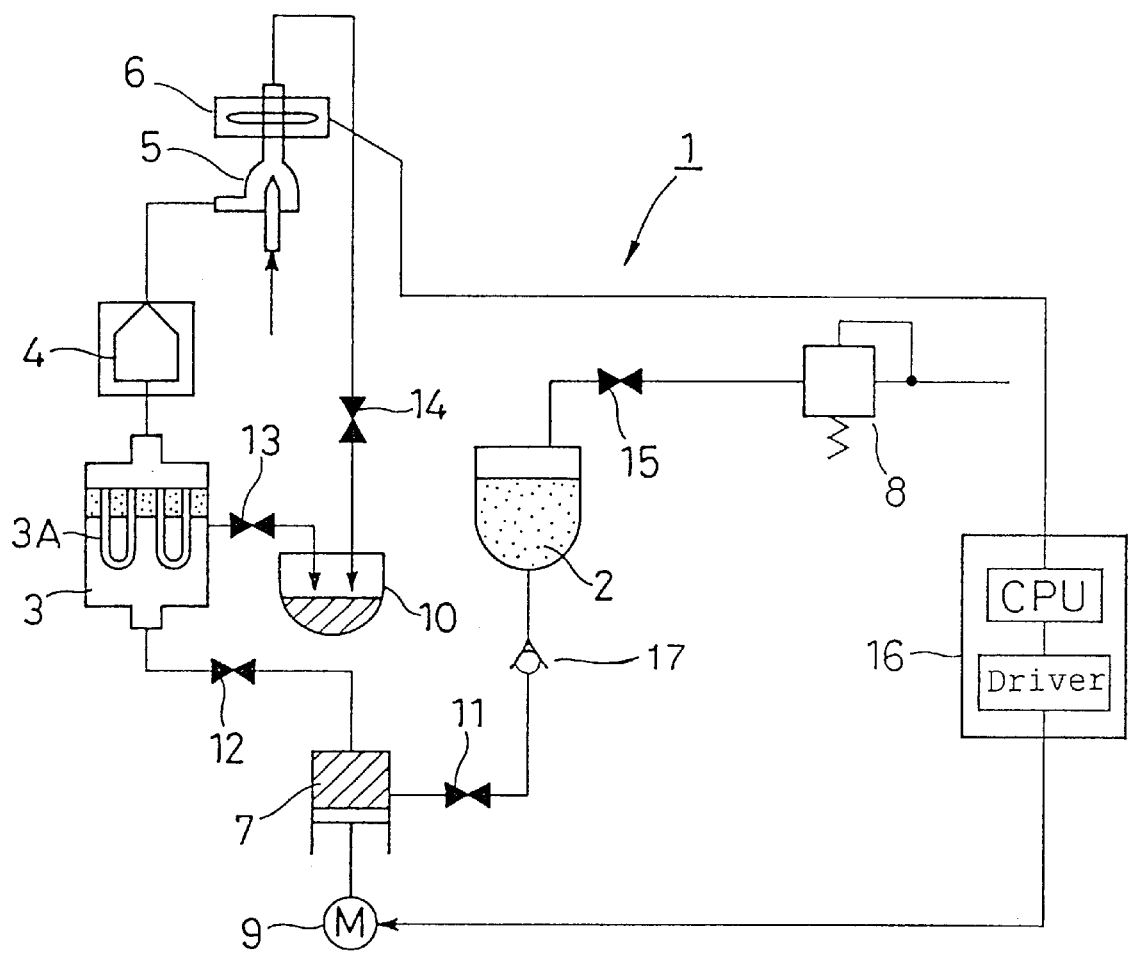
FIG. 1 is an explanatory view of an overall construction showing an embodiment of a flow cytometer according to the present invention.

Namely, in the present invention, the reliability of particle measurement can be increased by comparing a pulse width of a signal data obtained from a measurement of a particle in a sample, with a predetermined standard value to obtain a comparison value and monitoring a sheath liquid flow rate based on the comparison value. Further, since the sheath liquid flow rate is influenced not only by a pressure but also by a temperature, it is not possible to monitor the sheath liquid flow rate accurately by means of a pressure signal alone. However, according to the present invention, it is possible to monitor the sheath liquid flow rate accurately because the sheath liquid flow rate itself is detected.

Particles in a sample according to the present invention may be, for example, artificial particles (such as spherical silica particles or latex particles) and particles originating from an organism, namely, solid components in urine, blood, or the like (such as red blood cells, white blood cells, or casts).

In the present invention, the pulse width represents a period of time from the start of detection of a signal data of a particle until the end of the detection, and the signal data may be an electric signal obtained by photoelectric conversion of scattered light or fluorescence emitted from the particle by applying light to the particle.

The standard value according to the present invention represents a pulse width value of a signal data obtained by photoelectric conversion of scattered light or fluorescence emitted from the particle by applying light to the particle beforehand, or a pulse width value of a signal data obtained using a statistical technique by photoelectric conversion of scattered light or fluorescence emitted from that type of particles by applying light to the particles beforehand although the particle itself is not measured.

The monitoring section according to the present invention represents a constituent element which compares a pulse width of a signal data obtained by measuring a particle in a sample, with a predetermined standard value to obtain a comparison value and monitors the sheath liquid flow rate based on the comparison value. More specifically, the monitoring section may be provided with a storage circuit as a storage section for storing the preset standard value and the pulse width of the signal data obtained by the measurement, and a comparison circuit for comparing the standard value with the measured value, and may be further provided with a display section for displaying the values in characters, symbols, or the like on a display screen such as a liquid crystal display, and an alarming section for giving an alarm by sound or displaying an alarm in characters, symbols, or the like on a display screen such as a liquid crystal display if the value is out of a set range, for example, ±5% of the standard value.

Here, clogging may be delayed by providing a filter section for removing impurities in the sheath liquid between the sheath liquid supplying section and the measuring section for measuring the sample. Thus, in the particle measuring apparatus provided with a filter section, it is preferable that the time for exchanging the filter section may be alarmed by the above-mentioned alarming section if the comparison value is out of the set range.

Further, the present invention provides a particle measuring apparatus wherein the filter section is partitioned by a semipermeable membrane and includes a discharging outlet on a sheath liquid inlet side of the partitioned filter section near a sheath liquid outlet, whereby impurities such as bacteria and air bubbles attached to the semipermeable membrane are removed by pressurizing the sheath liquid from the sheath liquid outlet and discharging the pressurized sheath liquid from the discharging outlet.

In other words, in the present invention, the sheath liquid is pressurized from the sheath liquid outlet of the filter section in a direction opposite to that at the time of filtering the sheath liquid with the filter section, thereby removing through the discharging outlet the impurities such as bacteria and air bubbles attached to the semipermeable membrane on the sheath liquid inlet side in addition to monitoring the sheath liquid flow rate. This delays the decrease in the filtering efficiency of the semipermeable membrane and extends the life span of the filter section.

As a specific means for pressurizing the sheath liquid from the sheath liquid outlet of the filter section, it is preferable to provide a three-way switching valve between the measuring section and the sheath liquid outlet (lower pressure side) of the filter section partitioned by the semipermeable membrane, and to connect a pressurized air source (typically, 0.3 to 0.6 kg/cm$^2$) for switching and pressurizing the sheath liquid to a switching port, because the construction would be simple.

Also, as a semipermeable membrane of the filter section, a separating membrane which is typically called a precision filtration membrane, an ultrafiltration membrane, or a reverse osmosis membrane may be used, and the material for the semipermeable membrane may be an aromatic polyamide, allyl-alkylpolyamide/polyurea, polypiperazineamide, cellulose acetate, a cross-linked cellulose, a cross-linked polyether, sulphonated polysulphone, or the like. The shape of the semipermeable membrane is preferably a hollow thread membrane because a large filtration area is available with a compact construction.

As described above, the sheath liquid pressurized from the sheath liquid outlet side is discharged through the discharging outlet. Specifically, the pressurized sheath liquid is discharged, for example, from the discharging outlet through a discharging passageway to an exhaust liquid section. A solenoid opening/closing valve is disposed on the discharging passageway. The exhaust liquid section may also perform a function of an exhaust liquid section for accepting an exhaust liquid (for example, the sheath liquid and the sample liquid) discharged from the measuring section.

As described above, a specific control section is actually used for removing impurities such as bacteria and air bubbles attached to the semipermeable membrane. In other words, the control section pressurizes the sheath liquid from the sheath liquid outlet and issues an operation command to the pressurized air source, the three-way switching valve, the solenoid valve of the discharging passageway, and the like at a predetermined set time for discharging the pressurized sheath liquid through the discharging outlet, thereby automatically removing the attachments such as bacteria and air bubbles on the semipermeable membrane. This operation is preferably carried out automatically each time when a predetermined number of measurements have been carried out or when a predetermined number of days have passed or when the apparatus is shut down. The shutting-down of the apparatus represents an operation such as cleaning which is automatically carried out by the apparatus when the use of the apparatus is ended and the power supply is turned down.

Further, the particle measuring apparatus of the present invention may have a construction which compares a pulse width of the signal data obtained from a measurement of the particle in the sample, with a predetermined standard value to obtain a comparison value and operates to automatically remove impurities such as bacteria and air bubbles attached to the semipermeable membrane in addition to monitoring the flow rate of the sheath liquid if the comparison value is out of a predetermined set range.

In the present invention, the control mechanism section for controlling the flow rate of the sheath liquid represents a constituent element which supplies a pressure to the sheath liquid so that the measured value will be the standard value, for example, a device for controlling the operational velocity of a stepping motor of a sheath syringe. Further, by providing a liquid temperature adjusting section for adjusting the temperature of the sheath liquid which is flowing toward the measuring section, it is possible to maintain a liquid temperature, which is a factor giving an influence on the sheath flow rate, to be constant, and to accurately reflect the pressure of the pressure supplying section on the flow rate in the measuring section. Also, it is possible to control the sheath liquid flow rate in the measuring section by changing the liquid temperature based on the above-mentioned measured value and the standard value.

A detailed explanation will be given of the present invention based on embodiments shown by the drawings as follows. The present invention is not limited thereby.

Figure 2:
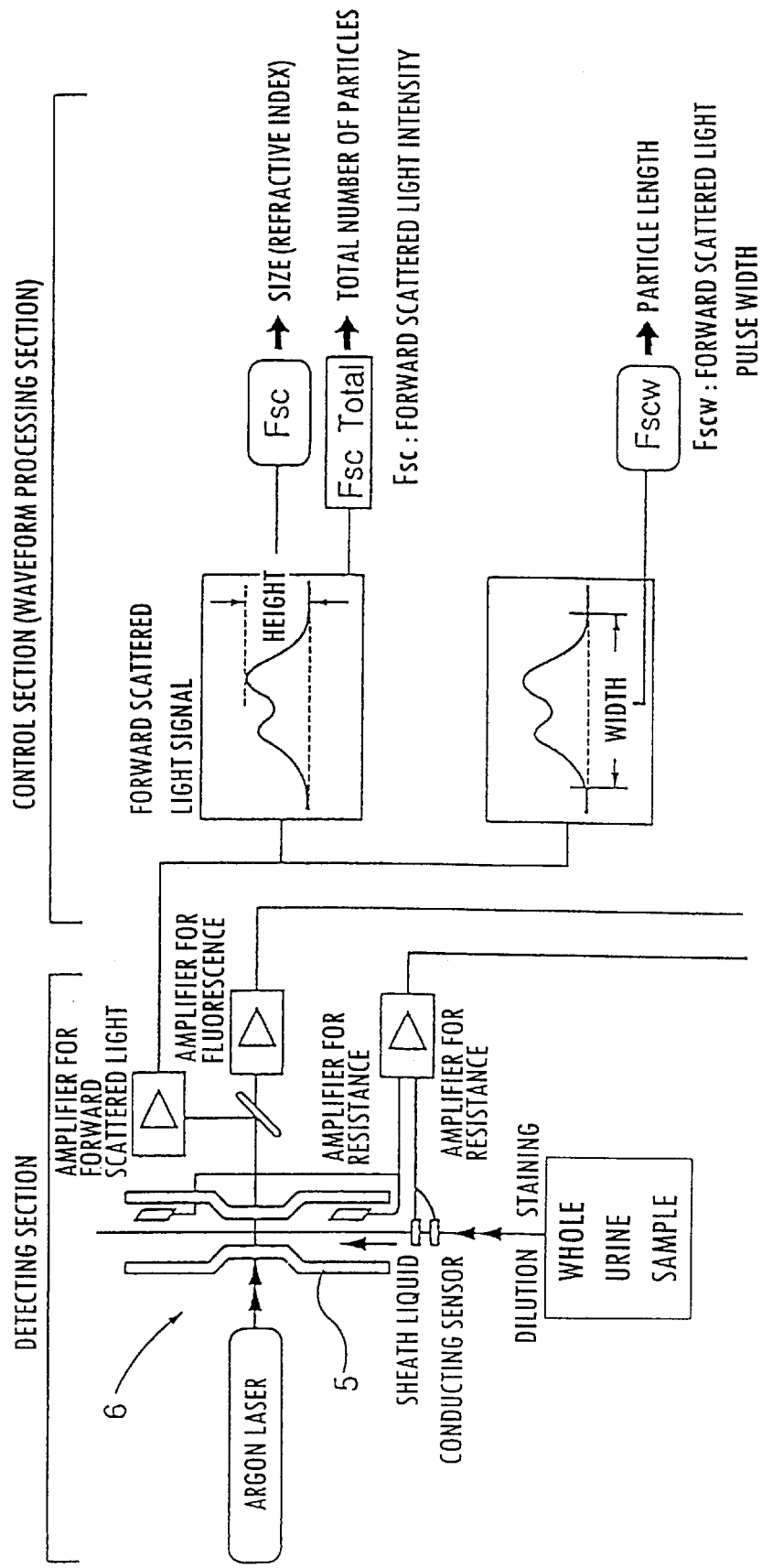
FIG. 2 is a view showing an enlarged essential part of FIG. 1 and explaining signals according to the present invention.

FIG. 1 is an explanatory view of an overall construction showing an embodiment of a flow cytometer according to the present invention. FIG. 2 is an explanatory view showing an enlarged essential part of FIG. 1.

Referring to FIG. 1, a flow cytometer 1 as a particle measuring apparatus for measuring particles (such as bacteria) in a sample (such as a urine stained with a fluorescent dye) mainly includes a sheath liquid pressurizing/supplying chamber 2 as a sheath liquid pressurizing section for pressurizing and supplying a sheath liquid (sheath flow liquid), a filter section 3 for removing impurities in the pressurized sheath liquid supplied from the sheath liquid pressurizing/supplying chamber 2, a sheath liquid heater 4 as a liquid temperature controlling section for adjusting the temperature of the sheath liquid from which the impurities have been removed, a flow cell 5 for surrounding the sample with the pressurized sheath liquid whose temperature has been adjusted and from which the impurities have been removed, thereby converging it into a narrow stream, a measuring section 6 disposed in the flow cell 5 for measuring the particles flowing in the sample, and a sheath liquid syringe 7 disposed between the sheath liquid pressurizing/supplying chamber 2 and the filter section 3 as a control mechanism section for controlling the flow rate of the pressurized sheath liquid to be supplied to the filter section 3.

Referring also to FIG. 1, the flow cytometer 1 further includes a regulator 8 for supplying a pressurized air to the sheath liquid pressurizing/supplying chamber 2 through the solenoid opening/closing valve 15, a stepping motor 9 for driving the sheath liquid syringe 7, an exhaust liquid chamber 10 for discharging the sample and the sheath liquid exiting out of the flow cell 5 and for discharging the impurities removed at the filter section 3 and floating on a higher pressure side of the filter section 3, and solenoid opening/closing valves 11, 12, 13, and 14. The reference numeral 16 represents a monitoring section which is specifically a control section including a microcomputer and a driver. The monitoring section performs a function of comparing a pulse width of a signal data obtained from a measurement of a particle in a sample, with a predetermined standard value to obtain a comparison value and includes a storage section for storing the comparison value, a display section for displaying the comparison value, an alarming section, and a control section (not shown) for issuing a command to each of the alarming section and the sheath liquid syringe 7. The reference numeral 17 represents a back-flow check valve.

Next, an operation of the flow cytometer 1 having the above construction is hereafter explained.

Referring to FIGS. 1 and 2, a pressurized air (for example, 0.2 kg/cm$^2$) is supplied to the sheath liquid in the sheath liquid pressurizing/supplying chamber 2 by the regulator 8 through the solenoid opening/closing valve 15. The sheath liquid is then transported to the filter section 3 through the solenoid opening/closing valve 11, the sheath liquid syringe 7 and the solenoid opening/closing valve 12. Subsequently, impurities (such as bacteria and gas) are removed from the sheath liquid by means of the semipermeable membrane (for example, a group 3A of hollow thread membranes made of polyethylene resin) of the filter section 3, and the sheath liquid is warmed to about 35° C. (the temperature is adjusted) by flowing through the sheath liquid heater 4 to be directed to the flow cell 5.

On the other hand, the sample is supplied to the flow cell 5 from the sample syringe (not shown) and is surrounded by the sheath liquid to converge into a narrow stream. At this state, particles (bacteria) flowing in the sample are measured by the measuring section 6. Namely, a laser beam (such as an argon laser beam) is applied from a light emitting element to the above converged flow at an appropriate time. The forward scattered light and the fluorescence, which are generated when a solid component in the urine is irradiated with the laser beam, are detected by the photodiode and the photomultiplier (none shown) as photoreceptors. A pulse waveform obtained by the above detection is subjected to appropriate image processing in the control section 16, whereby the particles in the sample are classified and measured. The sheath liquid and the sample having finished through the measurement and flowed out of the flow cell 5 are discharged to the exhaust liquid chamber 10 through the solenoid opening/closing valve 14.

An example is now given in which a UF check, which is an artificial particle manufactured by Toa Medical Electronics, Co., Ltd., is used as an example of a particle with a known size.

Figure 3:
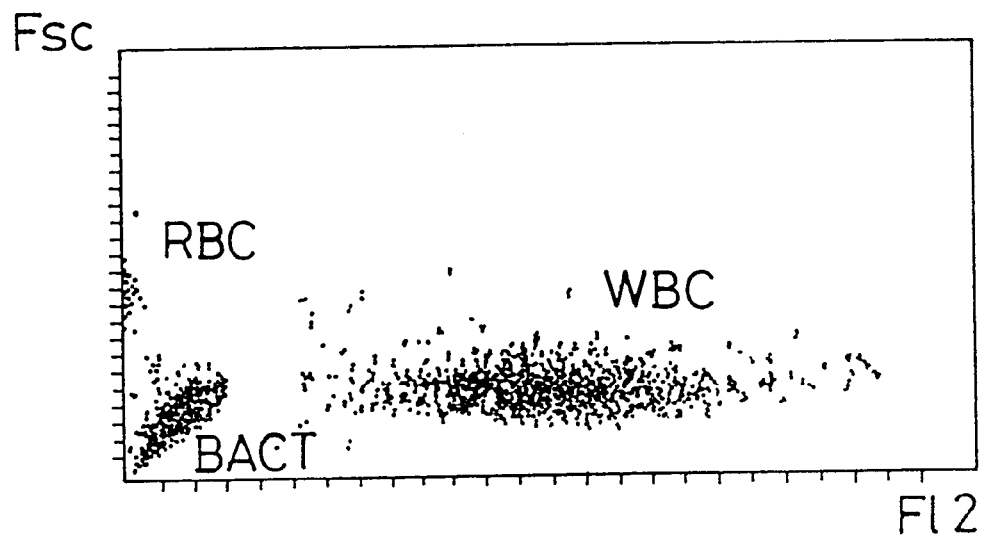
FIG. 3 is a two-dimensional scattergram of a forward scattered light intensity and a fluorescence intensity obtained by using a UF check according to the present invention.

A scattergram obtained by measurement of the UF check is given in FIG. 3. If particles of one of the classified groups therein, for example particles in the red blood cell (RBC) region, are to be utilized, an average value of a histogram of a forward scattered light pulse width (Fscw) of the particles classified as red blood cells (RBC) is determined by means of an analyzing algorithm.

The average value is then compared with a standard value inputted beforehand and, if the comparison value obtained by the comparison is out of a predetermined range, an alarm is given to prompt the user to exchange the filter (the function of the alarming section). Further, it is preferable to provide a function for controlling the sheath liquid flow rate (function of the control mechanism section) so that the comparison value will be 100%.

This method can be carried out also by using urine as the sample. Further, the type and the number of types of particles can be varied by making a suitable modification to the analyzing algorithm provided that the sizes of the particles are within a range of measurement.

Next, an example of a method is explained in which a statistical technique is employed.

Figure 4:
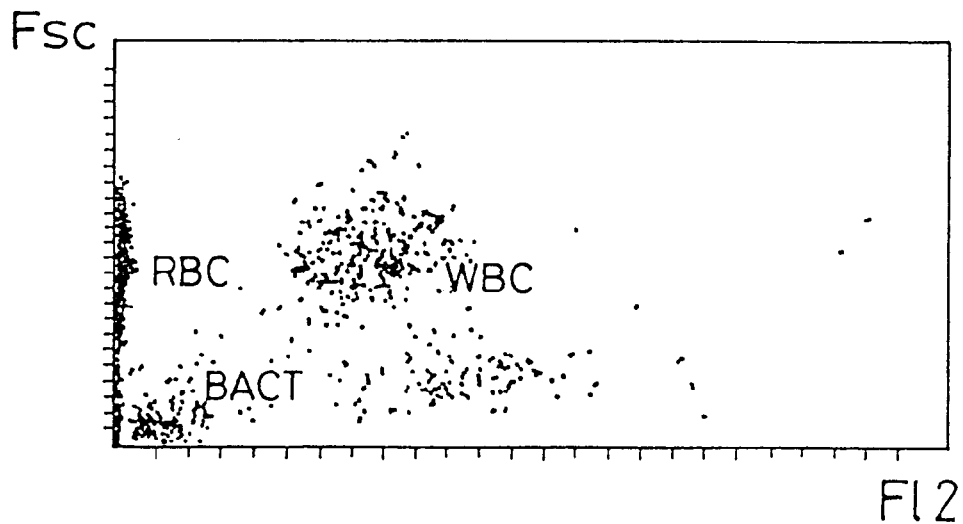
FIG. 4 is a two-dimensional scattergram of a forward scattered light intensity and a fluorescence intensity obtained by using a urine specimen according to the present invention.

FIG. 4 is a two-dimensional scattergram of a forward scattered light intensity and a fluorescence intensity obtained by using a urine specimen.

Figure 5:
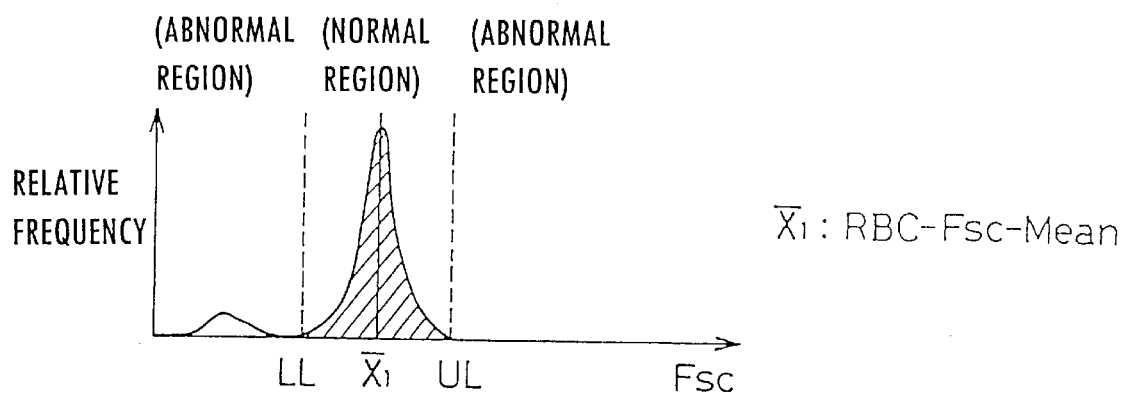
FIG. 5 is a relative frequency distribution diagram of RBC particles with respect to forward scattered light intensity (Fsc) according to the present invention.
Figure 6:
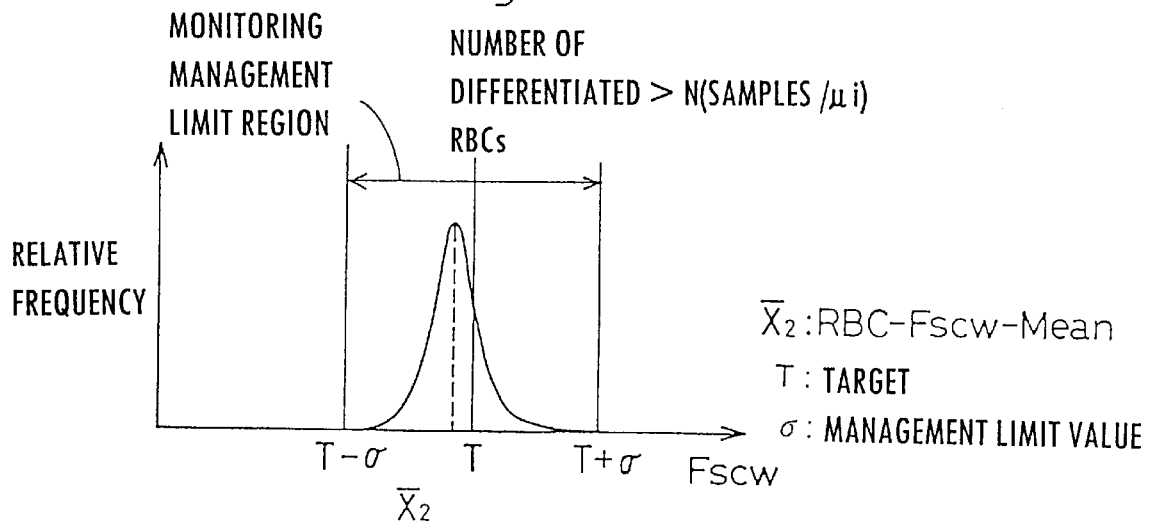
FIG. 6 is a relative frequency distribution diagram of normal RBC particles with respect to forward scattered light pulse width (Fscw) according to the present invention.

An example is explained in which a urine is used as the sample and red blood cells are used as one of the classified groups. Referring to FIG. 3, particles classified as red blood cells (RBC) by an analyzing algorithm are taken out. A histogram of the forward scattered light intensity (Fsc) of the particles is drawn, and red blood cells which are hemolyzed, contracted, or expanded are removed by using two constants (LL and UL) in FIG. 5.

Then, the control section determines whether the number of differentiated red blood cells exceeds a predetermined standard value (for example, 15/µ liter). If the number exceeds the standard value, an average value of the forward scattered light pulse width of these red blood cells is determined.

With respect to this average value, a predetermined number of daily measured specimens (for example, 20 specimens) are grouped as a batch, and a change in the measurement of the average value is monitored batch by batch. Namely, although the value for each specimen is not known beforehand, an effect of continuously monitoring the value during the measurement can be provided by regarding it as a value of a group.

With respect to a sudden abnormal value, its influence can be minimized by giving a small weight to values isolated from an average by using a weighted moving average method.

An example of this calculation is as follows:

$$X_M(i) = X_M(i-1) +$$

$$\mathrm{SGN}\left\{\sum_{J=1}^{N} \mathrm{SGN}[X(j,i) - X_M(i-1)]\sqrt{|X(j,i) - X_M(i-1)|}\right\} \cdot F$$

$$F = \left\{\frac{\sum_{J=1}^{N} \mathrm{SGN}|X(j,i) - X_M(i-1)|\sqrt{|X(j,i) - X_M(i-1)|}}{N}\right\}^2$$

Figure 7:
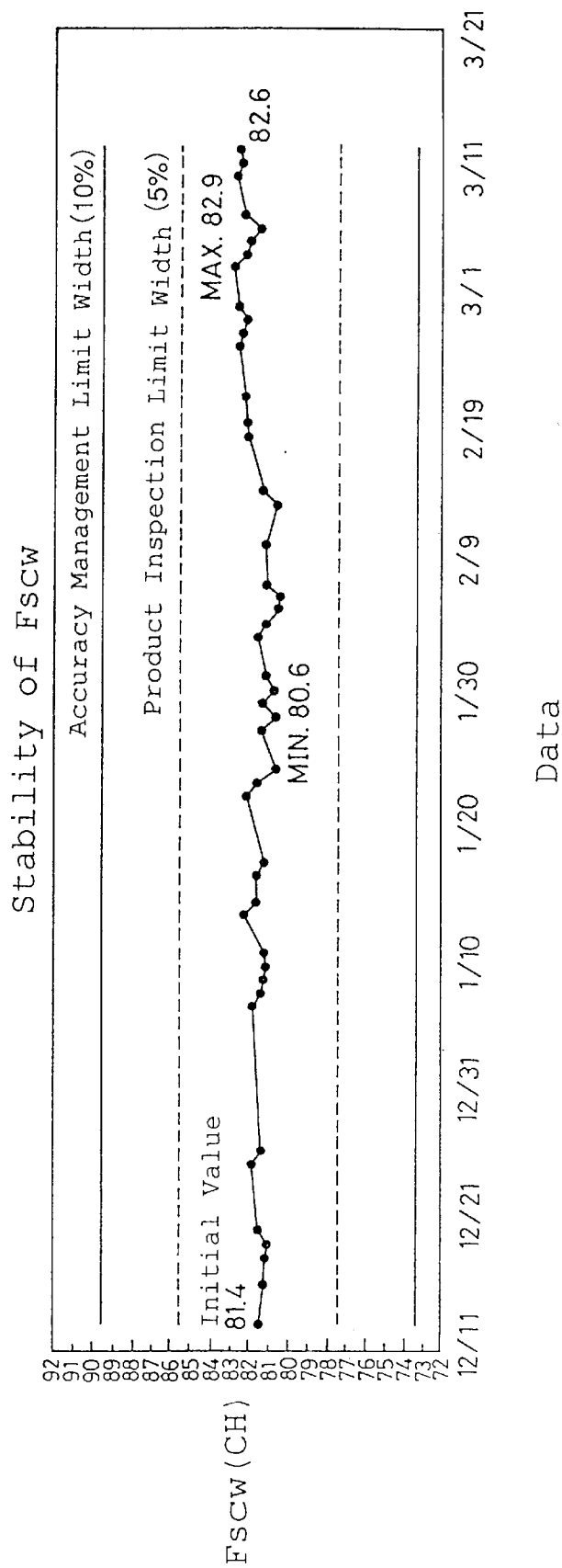
FIG. 7 is a graph showing a time-sequential change of sensitivity of forward scattered light pulse width (Fscw) of RBC particles according to the present invention.
Figure 8:
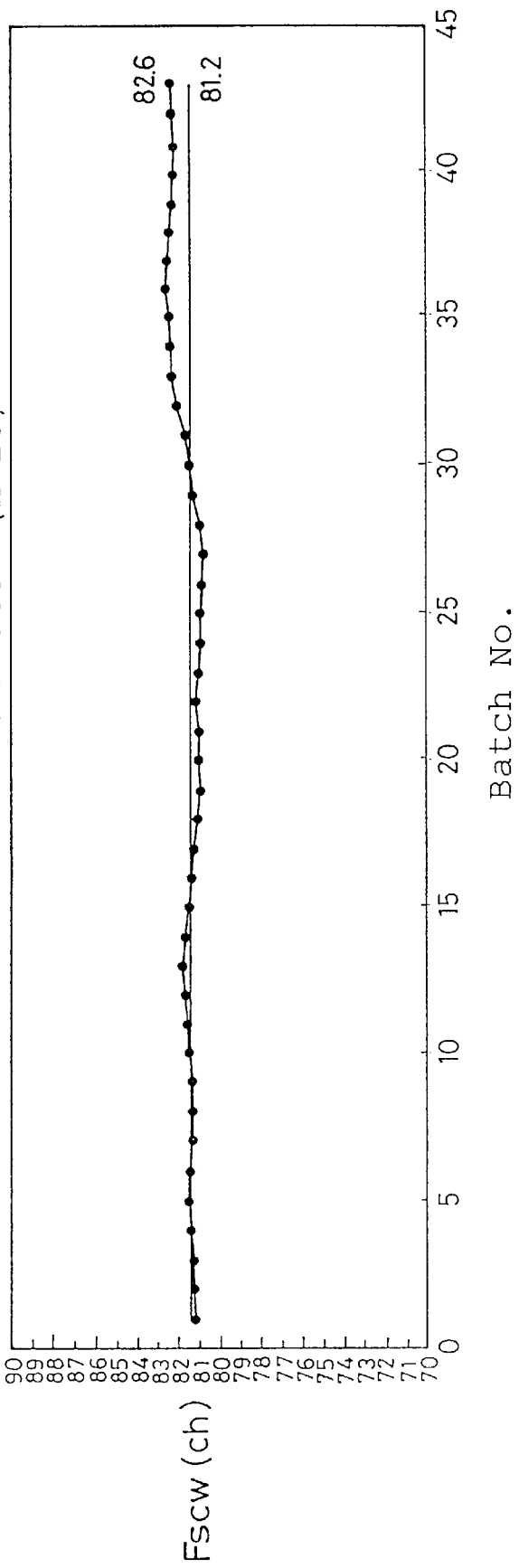
FIG. 8 is a graph showing a transition of an average value for each batch (n=20) of forward scattered light pulse width (Fscw) of RBC particles according to the present invention.

$X_M(i)$: $X_M$ of the $i_{th}$ batch
$X_M(i-1)$: $X_M$ of the $(i-1)_{th}$ batch
$X(j,i)$: $j_{th}$ measurement value in the $i_{th}$ batch
SGN: a sign in the parenthesis
N: number of samples for each batch By using an average ($X_M$) of the previous batch as the known value, a process similar to the above-mentioned example may be carried out (see FIGS. 7 and 8).

As described above, according to the flow cytometer 1, the reliability of particle measurement can be increased by comparing a pulse width of a signal data obtained from a measurement of a particle in a sample, with a predetermined standard value to obtain a comparison value and monitoring a sheath liquid flow rate based on the comparison value. Further, since the sheath liquid flow rate is influenced not only by a pressure but also by a temperature, it is not possible to monitor the sheath liquid flow rate accurately by means of a pressure signal alone. However, according to the flow cytometer 1, it is possible to monitor the sheath liquid flow rate accurately because the sheath liquid flow rate itself is detected.

Figure 9:
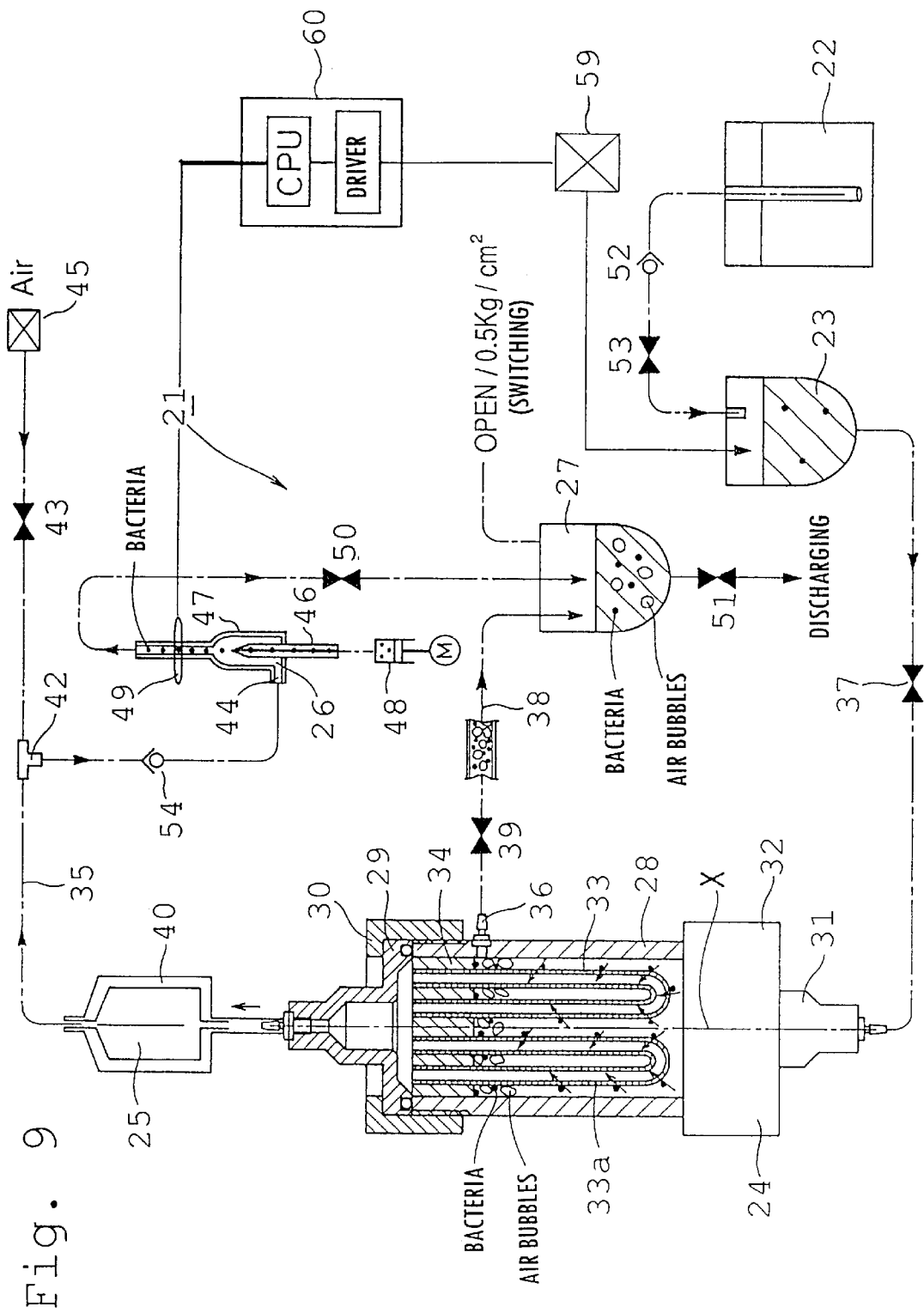
FIG. 9 is an explanatory view of an overall construction showing another embodiment of a flow cytometer according to the present invention.

FIG. 9 is an explanatory view of an overall construction showing another embodiment of a flow cytometer according to the present invention.

Referring to FIG. 9, a flow cytometer 21 as a particle measuring apparatus (or a particle counting apparatus) is intended to measure particles (such as bacteria) in a sample solution (urine stained with a fluorescent dye). The flow cytometer 21 mainly includes a sheath liquid container 22, a sheath liquid pressurizing chamber 23 as a sheath liquid pressurizing section, a filter section (bacteria removing filter) 24, a sheath liquid heater 25, a flow cell 26 as a measuring section, an exhaust liquid chamber 27 as an exhaust liquid section, and a control section 60. The control section 60 is different from the control section (monitoring section) 16 shown in FIGS. 1 and 2 only in that the control section 60 issues an operation command to the sheath liquid pressurizing chamber 23 through the pressurized air supplying section 59 while the control section 16 issues an operation command to the sheath liquid syringe 7 through the stepping motor 9 so as to control the flow rate of the sheath liquid. Accordingly, an explanation on the construction and operation of the control section 60 will be omitted here.

The filter section 24 includes a cylinder section 28 having a vertical central axis X, an upper cap 29, a coupling thereof 30, a lower cap 31, a coupling thereof 32, a group 33 of numerous hollow thread membranes (made of polyethylene resin) as a semipermeable membrane, a sealing member 34 for sealing and fixing the group of hollow thread membranes to an upper portion of the cylinder section 28, and a discharging section 36 extending outward from the cylinder section 28.

Here, the group 33 of the hollow thread membranes is partitioned so that each hollow thread membrane (for example, 33a) is bent to have a U-shape in the cylinder section 28 and sealed at both ends thereof by the sealing member 34, whereby an outside of the hollow thread membrane is a higher pressure side and an inside of the hollow thread membrane is a lower pressure side. The sheath liquid pressurizing chamber 23 is connected to the higher pressure side of the cylinder section 28 through a solenoid opening/closing valve 37, and the sheath liquid heater 25 is connected to the lower pressure side of the cylinder section 28.

The discharging section 36 includes a discharging passageway 38 extending from the discharging outlet 36 at an upper portion of the higher pressure side of the cylinder section 28 to the exhaust liquid chamber 27, and a solenoid opening/closing valve 39 disposed in the discharging passageway 38. The sheath liquid heater 25 includes a warming chamber 40 for warming the sheath liquid and a surface heater (not shown) integrally wound around the warming chamber 40. An inlet of the warming chamber 40 is connected to the lower side of the filter section 24, and an outlet of the warming chamber 40 is connected to a sheath liquid inlet 44 of a later-mentioned flow cell 26 through a flow passageway 35 via a three-way switching valve 42. The other port of the three-way switching valve 42 is connected to a pressurized air source 45 as a sheath liquid reverse-pressurizing section through a solenoid switching valve 43.

The flow cell 26 has a sheath liquid inlet 44 and a sample liquid inlet 46, and includes a flow cell body 47 for surrounding the sample liquid introduced from the sample liquid inlet 46 with the sheath liquid introduced from the sheath liquid inlet 44 and converging them into a narrow stream, a sample syringe 48 connected to the sample liquid inlet 46, and a detector 49 for applying a laser beam to the above-mentioned converged narrow stream to detect the scattered light and the fluorescence thereof. The sheath liquid and the sample liquid flowing out of the flow cell body 47 are discharged into the exhaust liquid chamber 27 through a solenoid opening/closing valve 50. A solenoid opening/closing valve 51 is disposed at a discharging outlet of the exhaust liquid chamber 27; a back-flow check valve 52 is disposed between the sheath liquid bottle 22 and the sheath liquid pressurizing chamber 23; a solenoid opening/ closing valve 53 is disposed between the back-flow check valve 52 and the sheath liquid pressurizing chamber 23; and a back-flow check valve 54 is disposed between the three-way switching valve 42 and the sheath liquid inlet 44.

Next, an operation of the flow cytometer 21 having the above construction is hereafter explained.

The sheath liquid introduced from the sheath liquid bottle 22 through the back-flow check valve 52 and the solenoid opening/closing valve 53 to the sheath liquid pressurizing chamber 23 is pressurized by a supply of a pressurized air (about 0.2 kg/cm$^2$) and is supplied to the higher pressure side of the hollow thread membrane group 33 of the filter section 24 through the solenoid opening/closing valve 37. Impurities (such as bacteria and gas) are removed by means of the hollow thread membrane group 33, and the sheath liquid is warmed to about 35° C. (the temperature is adjusted) by means of the sheath liquid heater 25 and is supplied to the sheath liquid inlet 44 of the flow cell 26 through the three-way switching valve 42.

On the other hand, the sample liquid is supplied from the sample syringe 48 and is surrounded by the sheath liquid to be converged into a narrow stream, whereby particles (bacteria) flowing in the sample liquid are measured by the detector 49. Namely, a laser beam (such as an argon laser beam) is applied to the above-mentioned narrow stream, whereby a photodiode and a photomultiplier (none shown) detect a forward scattered light and a fluorescence generated when the laser beam impinges upon a solid component in the urine. Signals obtained by the above detection are subjected to image processing at an appropriate time to classify and count the bacteria. The sheath liquid and the sample liquid having finished through the measurement and flowed out of the flow cell 26 are discharged into the exhaust liquid chamber 27 through the solenoid opening/closing valve 50.

When the measurement by the flow cytometer 21 is finished, the solenoid opening/closing valve 39 is opened and the three-way switching valve 42 is switched to operate the pressurized air source 45 (about 0.5 kg/cm$^2$), whereby the sheath liquid on the lower pressure side of the filter section 24 partitioned by the hollow thread membrane group 33 is pressurized in a reverse direction to separate and remove the clogging particles on the hollow thread membrane group 33 to the higher pressure side, and the removed particles and the gas floating thereabout are discharged into the exhaust liquid chamber 27 through the discharging passageway 38. Thus, by separating and removing the clogging particles on the hollow thread membrane group 33, the life span of the filter section 24 can be extended. Also, since the floating gas can be removed, the pressure from the sheath liquid pressurizing chamber 23 is transmitted to the sheath liquid without being absorbed by the floating gas, so that the flow rate of the sheath liquid in the flow cell 26 is stabilized (preventing decrease in the flow rate), making it possible to carry out a highly accurate measurement. Here, the separation and removal of the clogging particles may be carried out not only each time after the measurement is finished but also periodically while the measurement is being carried out or before the measurement is started. Also, bacteria and gas floating around a surface on the higher pressure side of the hollow thread membrane group 33 may be removed and discharged by simply opening the solenoid opening/closing valve 39 of the discharging passageway 38 for a predetermined period of time without operating the pressurized air source 45.

The material for the hollow thread membrane (or hollow thread) may be an olefinic resin, for example, a polyethylene resin as described above. The bore diameter of the hollow thread membrane must be generally 0.3 μm or less, preferably about 0.1 μm, in order to remove the bacteria. The effective surface area of the filter is suitably about 3000 to 5000 cm$^2$. The dimension of the filter is preferably such that its length is more than twice its diameter. A longer length is more preferred. For example, the filter may have a diameter of 40 mm and a length of 120 mm.

This is because, if the effective surface area of the filter remains the same, clogging of the filter can be prevented more and the life span of the filter will be longer (the initial rate of change in the flow rate can be reduced) accordingly as hollow thread membranes having a longer dimension are used and the number of hollow thread membranes decreases.

As shown above, according to the flow cytometer 21, the sheath liquid is pressurized from the sheath liquid outlet of the filter section in a direction opposite to the direction in which the sheath liquid is filtered by the filter section, whereby it is possible to remove through the discharging outlet the impurities such as bacteria and air bubbles attached to the surface of the semipermeable membrane on the sheath liquid inlet side in addition to monitoring the sheath liquid flow rate. This can delay the decrease in the filtration efficiency of the semipermeable membrane and extend the life span of the filter section.

Thus, the flow cytometer 21 shown in FIG. 9 is different from the flow cytometer 1 shown in FIG. 2 in that the control section 60 compares the pulse width of the signal data obtained by measurement of the particle in the sample, with the predetermined standard value and issues a command to open the solenoid opening/closing valve 39 and to switch the three-way switching valve 42 to operate the pressurized air source 45 if the comparison value obtained by the above comparison is out of a predetermined set range, whereby the sheath liquid is pressurized from the sheath liquid outlet of the filter section to automatically remove the impurities such as bacteria and air bubbles attached to the semipermeable membrane in addition to monitoring the sheath liquid flow rate, thus delaying the decrease in the filtration efficiency of the semipermeable membrane and extending the life span of the filter section.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What is claimed is:

1. A particle measuring apparatus comprising:
   a flow section for surrounding a sample with a sheath liquid to hydrodynamically converge and flow the sample and the sheath liquid to provide converged liquid;
   a measurement section including only a single light emitter for measuring a particle in the sample of the converged liquid to provide a signal data of the sample; and
   a monitoring section for comparing a pulse width of the signal data with a predetermined value to obtain a comparison value and monitoring a flow rate of the sheath liquid based on the comparison value.

2. The particle measuring apparatus of claim 1 further including a filter section for removing impurities in the sheath liquid, the monitoring section comprising an alarming section for providing an alarm warning to exchange the filter section if the comparison value is out of a predetermined set range.

3. The particle measuring apparatus of claim 1 wherein impurities attached to a semipermeable membrane are automatically removed each time after a predetermined number of measurements have been carried out or after a predetermined number of days have passed.

4. The particle measuring apparatus of claim 1 wherein impurities attached to a semipermeable membrane are automatically removed each time when the particle measuring apparatus is shut down.

5. The particle measuring apparatus of claim 1 wherein impurities attached to a semipermeable membrane are automatically removed if the comparison value is out of a predetermined set range.

6. The particle measuring apparatus of claim 1 wherein the monitoring section comprises an alarming section for providing an alarm if the comparison value is out of a predetermined set range.

7. The particle measuring apparatus of claim 1 wherein the particle in the sample is an artificial particle.

8. The particle measuring apparatus of claim 1 wherein a standard value is the pulse width of a signal data obtained using a statistical technique.

9. The particle measuring apparatus of claim 1, further comprising:
 a sheath liquid supply section for supplying sheath liquid; and
 a filter section for filtering the supplied sheath liquid to provide filtered sheath liquid to said flow section as the sheath liquid.

10. The particle measuring apparatus of claim 9, wherein said filter section comprises:
 a semipermeable membrane that partitions said filter section;
 a sheath liquid outlet on a sheath liquid outlet side of said semipermeable membrane;
 a sheath liquid inlet on a sheath liquid inlet side of said semipermeable membrane; and
 a discharge outlet on the sheath liquid inlet side of said semipermeable membrane,
 the particle measuring apparatus further comprising a sheath liquid discharge pressurizing section for charging pressurized sheath liquid into said sheath liquid outlet to discharge impurities attached to said semipermeable membrane from said filter section via said discharge outlet.

11. The particle measuring apparatus of claim 1, further comprising:
 a sheath liquid pressurizing section for changing a pressure of the sheath liquid provided to said flow section based on the comparison value.

12. The particle measurement apparatus of claim 1, wherein said measurement section comprises:
 a laser source for transmitting laser light through the converged liquid, the signal data comprising a forward scattered light pulse.

* * * * *